United States Patent [19]

Bass et al.

[11] Patent Number: 5,209,776
[45] Date of Patent: May 11, 1993

[54] TISSUE BONDING AND SEALING COMPOSITION AND METHOD OF USING THE SAME

[75] Inventors: Lawrence S. Bass, Little Neck; Steven K. Libutti, Lido Beach; Alexander M. Eaton, New York, all of N.Y.

[73] Assignee: The Trustees of Columbia University in the City of New York, New York, N.Y.

[21] Appl. No.: 560,069

[22] Filed: Jul. 27, 1990

[51] Int. Cl.$^5$ .............................................. C08L 89/00
[52] U.S. Cl. ................................... 106/124; 106/126; 106/128; 106/135; 106/137; 106/157; 106/158; 106/161; 514/773; 514/776; 606/214
[58] Field of Search ............... 106/124, 126, 128, 135, 106/137, 157, 158, 161, 162, 178, 217, 287.2, 287.21, 287.25; 514/773, 776; 606/214

[56] References Cited

U.S. PATENT DOCUMENTS

| | | | |
|---|---|---|---|
| 565,361 | 8/1896 | Link | 106/126 |
| 1,810,484 | 6/1931 | Kumli | 106/135 |
| 2,195,926 | 4/1940 | Hoskins | 106/126 |
| 2,214,231 | 10/1936 | Ketter | 106/126 |
| 2,277,486 | 3/1942 | Gewehyr | 106/158 |
| 3,398,007 | 8/1968 | Pillerdorf et al. | 106/128 |
| 3,438,374 | 4/1969 | Falb et al. | |
| 4,122,853 | 10/1978 | Smith | |
| 4,139,395 | 2/1979 | Dunlap | 106/157 |
| 4,350,629 | 9/1982 | Yannes et al. | 106/157 |
| 4,362,567 | 12/1982 | Shwarz et al. | |
| 4,414,976 | 11/1983 | Schwarz et al. | |
| 4,451,397 | 5/1984 | Huc et al. | 106/157 |
| 4,550,238 | 10/1985 | Van Herle et al. | |
| 4,625,724 | 12/1986 | Suzuki | |
| 4,633,870 | 1/1987 | Saver | |
| 4,657,820 | 4/1987 | Halpern et al. | 106/157 |
| 4,672,969 | 6/1987 | Dew | |
| 4,676,790 | 6/1987 | Kern | |
| 4,782,819 | 11/1988 | Adair | |
| 4,818,291 | 4/1989 | Iwatsuki et al. | |
| 4,854,320 | 8/1989 | Dew et al. | |
| 4,909,251 | 3/1990 | Seelich | |
| 5,015,677 | 5/1991 | Benedict et al. | 106/157 |

FOREIGN PATENT DOCUMENTS 62-45678  2/1987  Japan ..................... 106/135

OTHER PUBLICATIONS

K. K. Jain "Repair of small blood vessels with the neodyomium yag laser" Surgery vol. 85 No. 6 pp. 684–688 (Jun. 1979).
R. L. Burleson et al "Fibrin Adherence to biologic tissues" J. Surg. Research 25, 523–529 (Dec. 1978).
Khalid J. Awan et al "use of Isobutyl-2-Cyanoacrylate tissue adhesive" Annals of Opth pp. 851–853 (Aug. 1974).
J. A. Fayez et al "Tubal Microsurgery with the Carbon dioxide Laser" Am. J. obster. Gynecol 146/4 (Jun. 1983).
G. F. Gestring et al "Autologoos Fibrinogen for tissue adhesion . . . " Vas. Surg pp. 294–304 (Sep. 1983).
F. X. Brunner "Histological findings in sutured and fibrin-glued Microvascular Anastomosis" A. Otor. 240:311–318 (Jan. 1984).
J. A. Fayez et al "Comparison of Tubal Surgery with the $CO_2$ Laser . . . " Fert. and Ster. vol. 40 No. 4 (Oct. 1983).
J. K. Choe et al "Clinical and Histological evaluation of Laser Reanastomosis . . . " Fert. and Ster. vol. 41 No. 5 (May 1984).
E. L. Smith et al "Principles of Biochemistry" 7th Edition pp. 7 and 229 (Jan. 1983).
R. R. Krueger et al "Argon Laser Coagulation of Blood for the Anastomosis of small vessels" Laser in Surg.±Med 5:55–60 (May 1985).

(List continued on next page.)

Primary Examiner—David Brunsman
Attorney, Agent, or Firm—John P. White

[57] ABSTRACT

Disclosed is a composition for bonding separated tissues together or for coating tissues or prosthetic materials including at least one natural or synthetic peptide and at least one support material which may be activated by energy.

22 Claims, No Drawings

OTHER PUBLICATIONS

K. H. Siedentor et al "Autologous Fibrin Tissue Adhesive" Laryngoscope 95:1074–1076 (Sep. 1985).
J. S. Sauer et al "Bursting Pressures of $CO_2$ Laser—Welded Rabbit Ileum" Lasers in Surg±Med 6:106–109 (Jun. 1986).
J. W. Baker et al "A technique for spray application of Fibrin Glue . . . " Ann. Thorac. Surg 43:564–65 (May 1987).
D. J. Coleman et al "A Biologic Tissue Adhesive for vitreoretinal surgery" Retina vol. 8 No. 4:250–256 (Apr. 1988).
A. Hjortrup et al "Fibrin Adhesive versus sutured Anastomosis . . . " Br. J. Surg vol. 73:760–761 (Sep. 1986).
T. T. Liesegang et al "The use of Hydroxypropyl Methyl-Cellulose . . . " Am. J. of Opth. 102:723–726 (Dec. 1986).
A. Henrick et al "Organic Tissue Glue in the Closure of Cataract incisions" J. Cat. Ref. Surg vol. 13:551–53 (Sep. 1987).
S. R. Gundry et al "A quantitative and Qualitative comparison of Fibrin Glue Albumin———" J. Surg. Res. 43:75–77 (Jul. 1987).
M. P. Fried et al "Head±Neck applications of the milliwat Laser" Lasers in surg±Med. 7:46–50 (Jan. 1987).
J. E. Bailes et al "Review of Tissue Welding Application in Neurosurgery" Microsurgery 8:242–244 (Dec. 1987).
D. P. Poppas et al "Laser welding in Urethral surgery . . . " J. Uralogy vol. 139:415–417 (Dec. 1988).
D. Miller et al "Healon a guide to its use in Opthalmic surgery" pp. 5–28 (Dec. 1983).
D. F. Thompson et al "Fibrin Glue: A review of its Preparation, Efficacy and adverse effects———" Drug. Int.±Clin. Pharm 22:946–951 (Dec. 1988).
A. F. S. Flemming et al "Laser assisted Microvascular Anastomosis———" Br. J. Plast Surg 41: 378–388 (Dec. 1988).
B. A. Lowe et al "Vasovasostomy in the Murine Vas Deferens———" Lasers in Surg±Med 8:377–380 (Aug. 1988).

G. E. Kopchock et al "$CO_2$ and Argon Laser Vascular Welding———" Laser in Surg±Med 8:584–588 (Aug. 1988).
H. Zauberman et al "Use of Fibrin Glue in ocular Surgery" Opth. Surg vol. 19 No. 2:132–133 (Feb. 1988).
Su Wang et al "Effect of blood bonding on Bursting Strength———" Microsurgery 9:10–13 (Sep. 1988).
S. Rochkind et al "Low-Energy $CO_2$ Laser Intestinal Anastomosis———" Laser in Surg±Med 8:579–583 (Aug. 1988).
R. A. White et al "Mechanism of Tissue Fusion in Argon Laser-welded———" Lasers in Surg±Med 8:83–89 (Aug. 1988).
L. W. Murray et al "Cross-linking of extra cellular matrix Proteins———" Lasers in Surg.±Med. 9:490–496 (Sep. 1989).
R. Moosdorf et al "Laser-Assisted Anastomosis of the Trachea———" V. Surg. pp. 51–58 (Jan. 1989).
J. S. Sauer et al "the first sutureless, Laser-welded, end-to end Bowel/Anastomosis" Lasers in surg.±Med. 9:70–73 (Sep. 1989).
P. T. O. Gilbert et al "Laser-Assisted Vasovasotomy" Lasers in Surg.±Med. 9:42–44 (Sep. 1989).
I. K. Arenberg et al "Autologous Fibrin Glue and Sealant———" OT. surg vol. 101 No. 6:709∝712 (Jun. 1989).
T. E. Emerson "Unique Features of Albumin; A brief review" Crit. Care Med. vol. 17 No. 7:690–693 (Jul. 1989).
G. S. Ganesan et al "Urethral Reconstruction using the Carbon Dioxide Laser———" J. Urol. vol. 142; 1139–1141 (Oct. 1989).
L. S. Bass et al "Sutureless Microvascular Anastomosis using the Yag Laser———" Microsurgery 10:189–193 (Oct. 1989).
M. C. Oz et al "Tissue soldering by use of indocyanine green———" J. Vasc. Surg. 718–725 11:5 (May 1990).
B. Jean et al "Target dyes in Ophthalmology Part I" Laser in light in Opth. vol. 3 No. 1 pp. 39–45 (Jan. 1990).
C. S. Kischkel et al "Target dyes in opthalmology Part II" Lasers in light in Opth. vol. 3 No. 1 pp. 47–52 (Jan. 1990).

TISSUE BONDING AND SEALING COMPOSITION AND METHOD OF USING THE SAME

FIELD OF THE INVENTION

The present invention is directed to a composition adapted to bond separated tissues together or to coat tissues or prosthetic materials to enhance strength and water tightness preferably upon the application of energy and particularly to a composition which is activated by a laser to form a strong, watertight biologically compatible bond or coating.

BACKGROUND OF THE INVENTION

All surgical disciplines are concerned with the repair of damaged tissues and vessels. Damage can be the result of direct trauma to the body or as part of a surgical procedure in which there is a separation of normally continuous tissue such as in vein or artery anastomoses. Regardless of the cause, proper repair of the tissue or blood vessel is an essential step in the positive outcome of surgery.

The joining of separated tissues has principally been performed by suturing or stapling in which the skilled hands of the surgeon stitch or staple the separated tissues together. This procedure not only requires significant skill but also is a slow, tedious process, particularly if extensive repair is required.

Suturing suffers from several other drawbacks which have complicated surgical procedures. First, leaks often develop at the ends of the joined tissues which can require resuturing. In addition, suturing itself is a trauma to the tissue which can cause additional damage and extend the healing period. Further there are occurrences of inflammation in vicinity of the sutures which can result in late failure of a repair or anastomosis.

As a result, efforts have focused on overcoming the difficulties associated with suturing by the development of sutureless repairs using surgical adhesives or glues which adhere to tissue surfaces and form a bond therebetween.

The most common tissue adhesive is fibrin adhesive or glue typically containing a concentrate of fibrinogen and thrombin. Immediately prior to application these agents are mixed together and react in a manner similar to the last stages of the clotting cascade to form a fibrin clot. The clot fills the space between the separated tissues until the tissue regenerates eliminating the space. Fibrin adhesive has been used in a variety of surgical procedures because it forms a strong bond between the tissues and is generally biocompatible. (See, for example, Dennis F. Thompson et al., "Fibrin Glue: A Review of its Preparation, Efficacy and Adverse Effects as a Topical Hemostat", *Drug Intell. Clin. Pharm.* vol. 22, pp. 946-952 (1988); and Richard L. Burleson et al., "Fibrin Adherence to Biologic Tissues", *J. Surg. Res.* vol. 25, pp. 523-529 (1978).

Fibrin adhesive, however, has significant drawbacks which has prevented its commercial use in the United States. In order to prepare commercial quantities of fibrin adhesive the components must be obtained from pooled human blood. There is therefore the possibility of infection from agents such as Hepatitis "B", HIV virus and others. Particularly in the United States, the threat of infection has outweighed the benefits of obtaining commercial quantities of fibrin adhesive. As a result, the production of fibrin adhesive has been limited to quantities obtained from a patient's own blood to reduce the risk of infection. (See, for example, Karl H. Siedentop et al., "Autologous Fibrin Tissue Adhesive", *Laryngoscope* vol. 95, pp. 1074-1076 (September, 1985) Gidon F. Gestring et al., "Autologous Fibrinogen for Tissue-Adhesion, Hemostasis and Embolization", *Vasc. Surg.* vol. 17 pp. 294-304 (1983) and D. Jackson Coleman et al., "A Biologic Tissue Adhesive for Vitreoretinal Surgery", *Retina* vol. 8 no. 4, pp. 250-256 (1988). These autologous procedures make the use of fibrin adhesive costly and time consuming and therefore of limited value.

Non-biological materials have been tried as surgical adhesives in an effort to reduce the risk of infection over adhesives obtained from pooled blood. Isobutyl-2-cyanoacrylate has been applied to separated tissues and has formed a solid watertight seal shortly after contact with the tissue. Khalid J. Awan et al., "Use of Isobutyl-2-Cyanoacrylate Tissue Adhesive in the Repair of Conjunctional Fistula in Filtering Procedures for Glaucoma", *Annals of Ophth.* pp. 851-853 (August, 1974). However, such adhesives have been criticized because they are irritating to tissues, difficult to apply and fail to form a permanent closure. Andrew Henrick et al., "Organic Tissue Glue in the Closure of Cataract Incisions", *J. CATARACT REFRACT. SURG.* vol. 13 pp. 551-553 (September, 1987).

Thus, surgical adhesives have not been successful in replacing the suture as the primary means of tissue and vessel repair.

Another approach to sutureless tissue repair is tissue welding. Tissue welding involves the bonding of tissues together using an energy source such as a laser beam. Several types of lasers have been found useful for tissue welding including Nd:YAG, $CO_2$, THC:YAG and Argon. Julian E. Bailes et al., "Review of Tissue Welding Applications in Neurosurgery", *Microsurgery* vol. 8 pp. 242-244 (1987); Rodney A. White et al., "Mechanism of Tissue Fusion in Argon Laser-Welded Vein-Artery Anastomoses", *Lasers in Surgery and Medicine* vol 8. pp. 83-89 (1988); Lawrence S. Bass et al., "Sutureless Microvascular Anastomoses using the THC:YAG Laser: A Preliminary Report", *Microsurgery* vol. 10 pp. 189-193 (1989), Masame Suzuki et al., U.S. Pat. No. 4,625,724, Jude S Sauer U.S. Pat. No. 4,633,870; Douglas Dew, U.S. Pat. Nos. 4,672,969 and 4,854,320, each incorporated herein by reference.

Tissue welding has been performed on a variety of tissues. For example, a carbon dioxide laser has been used in nerve tissue repair as described in Julian E. Bailes et al., *Microsurgery.* Tissue welding has successfully repaired intestinal tissue. Semion Rochkind et al., "Low-Energy $CO_2$ Laser Intestinal Anastomsis: An Experimental Study" *Lasers in Surgery and Medicine* vol. 8 pp. 579-583 (1988).

The use of lasers to directly weld tissues can eliminate about two-thirds of the time needed to repair damaged tissues or blood vessels. However, histological analysis of direct laser welds has shown transmural thermal injury at the site of the weld which adds to the trauma of the injury and surgery. In vascular anastomosis, this can lead to complicating aneurysm formation at the weld site which presents a threat to the healing process and in some cases may lead to internal bleeding and complications associated therewith. Furthermore, the welds produced by direct laser contact have been characterized by marginal strength. The welds are prone to leakage and can burst in some cases.

To overcome the problems of direct tissue welding efforts have been made to employ organic agents which improve weld strength and at least minimize trauma to the tissue brought on by direct contact with laser energy. Typically, these agents known as laser adhesives or glues absorb laser energy forming a weld which bonds separated tissues together. In some cases, the laser adhesive selectively absorbs the laser energy thereby reducing the risk of transmural thermal injury. For example, blood has been used as a welding agent in laser repair surgery to improve bond strength and arterial healing through early fibrin cross-linking. Su Wang et al, "Effect of Blood Bonding on Bursting Strength of Laser-Assisted Microvascular Anastomoses", *Microsurgery* vol 9 pp. 10–13 (1988). Egg white albumin has also been used as a laser glue. Dix P. Poppas et al., "Laser Welding in Urethral Surgery: Improved Results with a Protein Solder", *J. Urology* vol. 139 pp. 415–417 (February, 1988) and George S. Ganesan et al., "Urethral Reconstruction Using The Carbon Dioxide Laser: An Experimental Evaluation", *J. Urology* vol. 142 pp. 1139–1141 (October, 1989).

Despite these efforts, laser adhesives still suffer from deficiencies which make their universal application problematical. In particular, laser adhesives are difficult to apply to separated tissues. They are either in the form of semi-solids (e.g. fibrinogen) or liquid (e.g. albumin or blood). As a semi-solid, the product must be cut into strips and placed at the weld site. Quite often the solid strip will move during application requiring time consuming repositioning. Additionally, the strip may shrink when exposed to the laser beam and weld only a portion of the tissue. The unwelded portion may be large enough to permit the passage of blood. This requires the use of additional strips of welding material and time consuming repeat operations.

Liquid laser adhesives are disadvantageous because they can run off of the weld site and thus may also require repeat applications. In addition, conventional laser adhesives made of protein materials, such as fibrinogen, often form rigid welds which reduce the flexibility of the welded tissues, particularly welded blood vessels. If the vessel is subjected to normal pressure fluctuations which occur during the cardiac cycle, the unclamping of the blood vessel or when the patient moves suddenly, the weld can rupture causing internal bleeding and related complications.

It is therefore an object of the present invention to provide a composition which can form a strong, flexible biologically compatible bond between separated tissues preferably upon the application of energy such as a laser beam.

It is another object of the invention to provide a composition which can form a watertight, flexible seal in tissues or prosthetic materials.

It is still another object of the invention to provide a laser adhesive whose viscosity can be modified according to the desired application to facilitate placement of the composition at the tissue site.

It is still another object of the invention to provide a method of bonding separated tissues or coating tissues to form a watertight seal using a composition which is easy to handle, particularly during surgical procedures.

SUMMARY OF THE INVENTION

The present invention is directed to a composition suitable for bonding separated tissues together while maintaining sufficient flexibility to allow normal tissue function. The bonding of the separated tissues can be enhanced by the application of energy such as a laser beam. The composition may also be used to coat tissues or prosthetic materials to form a watertight seal.

The viscosity of the composition can be varied so that delivery, positioning, stability during welding and final elasticity and strength are appropriate for the selected application. Such attributes allow faster, more efficient surgical repair of damaged or weakened tissues than is possible with suturing or known sutureless procedures.

The composition prefarably in the form of a solution, most preferably an aqueous solution comprises a first component which provides the tensile strength necessary to keep the welded tissue together, joining the separated tissue or providing a watertight, flexible seal on a tissue or prosthetic or implant surface. The second component forming part of the composition is adapted to support the first component producing an improved degree of inter-relationship among the molecules of the first component. The second component may also contribute sufficient elasticity to enable the weld to move in unison with the tissue or vessel during its normal bodily functions.

The second component may also function as a viscosity modifier according to the end use of the composition by raising or lowering the viscosity. Optionally, a viscosity modifier and/or bonding enhancer may be added to the composition according to need. The resulting composition provides a tissue adhesive having excellent strength and superior handling characteristics. The composition is particularly suited for laser welding by forming a strong, uniform, elastic weld or coating.

The first component is selected from natural synthetic peptides enzymatically cleaved or shortened variants thereof and cross-linked derivatives thereof and mixtures thereof. Included among the peptides are structural proteins and serum proteins. Examples of proteins are albumin, $\alpha$-globulins, $\beta$-globulins, $\gamma$-globulins, transthyretin, collagen, elastin and fibronectin and coagulation factors including fibrinogen, fibrin and thrombin.

The second component is generally selected from compounds which support the first component such as by forming a matrix or gel or sol with the first component. These compounds are generally selected from proteoglycans including enzymatically cleaved or shortened variants, cross-linked derivatives or subunits thereof including glycosaminoglycans, saccharides and polyalcohols. The proteoglycans are preferably natural or synthetic non-cellular body matrix materials found in the interstices between cells such as hyaluronic acid, salts of hyaluronic acid including sodium hyaluronate, chondroitin sulfate, dermatin sulfate, keratin sulfate and heparin sulfate. The saccharides are preferably selected from oligosaccharides such as fructose and polysaccharides such as hydroxypropylmethylcellulose, dextrans and agarose. The preferred polyalcohol is glycerine.

The composition is prepared in a form ranging from a flowable liquid to a sol to a viscous gel depending upon the application and the concentration of components. For example, the composition is preferably employed in the form of a viscous gel for bonding of separated tissues. On the other hand, the formation of a watertight seal on tissues or prosthetic materials is most efficiently accomplished using a less viscous composition.

In some cases the combination of the peptide and support material will spontaneously form a weld. In other cases, it may be necessary to activate the composition with energy. In general, activation with energy rapidly accelarates the bonding process. The energy employed in the present invention must be capable of activating the composition in a manner which produces the desired bonding or coating characteristics.

The composition can be activated from a variety of energy sources. Thermal energy and sound energy may be used. Preferably, the energy has a wavelength in the electromagnetic spectrum selected from monochromatic coherent light, monochromatic non-coherent light, polychromatic coherent light and polychromatic non-coherent light or electrical energy, in a continuous or discontinuous fashion. Most preferred are the use of lasers including, but not limited to THC:YAG, Nd:YAG; argon, krypton, carbon dioxide, diode, dye and the Excimer lasers.

The composition of the present invention can additionally contain viscosity modifiers and bonding enhancers in accordance with the end use of the composition. For example, the addition of viscosity modifiers provides a composition with a viscosity particularly suited to tissues which are to be repaired or sealed. A composition having a high viscosity is preferably employed to bond separated tissues while lower viscosity compositions are best suited to form a coating for watertight sealing of continuous tissue masses and prosthetic materials such as Gortex vascular grafts and the like. Such viscosity modifiers include compounds previously mentioned which are non-cellular body matrix materials such as hyaluronic acid and salts thereof such as sodium hyaluronate, hydroxypropylmethyl cellulose, glycerine, dextrans, honey, sodium chondroitin sulfate and mixtures thereof.

Bonding enhancers may also be used to improve the bonding strength of the composition. Such compounds include polar dyes such as indocyanine green which form electrostatic, polar and non-polar bonds on the protein. Polyvalent cations, such as calcium may also serve this purpose by binding to the negatively charged moieties in the proteins, such as albumin, and the glycosaminoglycans such as hyaluronic acid and chondroitin sulfate.

The components of the composition are combined together in quantities which provide a desired bonding strength as well as a viscosity which is particularly adapted to the end use. In general, the amount of the peptide is in the range of from about 1 to 70% by weight, preferably about 8 to 35% by weight. The amount of support material varies depending on the support material chosen. Saccharides are typically employed in the range of from about 0.1 to 70% by weight. The amount of the and glycosaminoglycans is preferably from about 0.1 to 20% by weight. Polyalcohols such as glycerine may be employed in an amount of from about 10 to 90% by weight.

The amount of additives such as viscosity modifiers and bonding enhancers is generally no more than about 65% by weight.

The viscosity of the composition is chosen in accordance with the particular surgical procedure being performed. For bonding of separated tissues, a viscosity of from about 1,000 to 1,000,000 centipoise is advantageously employed, preferably in the range of from about 20,000 to 200,000 centipoise. A composition having a viscosity in the preferred range can be easily placed on the separated tissues by ejecting through a hypodermic syringe and spread out by moving the syringe tip. In this viscosity range, the composition does not run off the tissues and remains fixed even when energy is applied to form the tissue weld.

The composition preferably has a lower viscosity for applications requiring the formation of a watertight coating for sealing tissues or prosthetic materials. The preferred viscosity for coating is in the range of from 100 to 1,000 centipoise. The lower viscosity is preferred because the composition should be readily spreadable to efficiently cover the tissue or material to be coated.

In compositions containing hyaluronic acid, or other non-Newtonian fluids, the viscosity decreases with increasing shear forces. Accordingly, the viscosity of the composition can be modulated by alterating the shear forces present when the composition is applied to the surface. As an example, a composition which is very thick when it is stationary can be injected through a graft by injecting it at a rapid or high sheer rate to reduce its viscosity during the transit phase.

This property known as pseudoplasticity is also characteristic of blood. It is ideal for welding at sites that are not subject to shearing forces during the welding process. When the composition is being injected, shear forces are high, and the viscosity decreases. This allows for easy injection. After being deposited on the tissue, the shear forces drop to zero, and the viscosity of the composition increases correspondingly. As a result, the composition stays localized on the tissue in the area to be welded.

The composition of the present invention provides a tissue bond having high tensile strength, elasticity, deformability, water tightness, viscosity and adhesivity for a large variety of surgical procedures. The composition can also be used to coat implantable devices to enhance their strength and resistance to fluids, to seal pores in the weave of the material, and reduce thrombogenicity. The composition is easily reproducible, non-infectious and stays stable and therefore can be used with greater speed and reliability than known surgical adhesives.

DETAILED DESCRIPTION OF THE INVENTION

The composition of the present invention can be used to bond separated tissues together and to coat continuous tissue masses or prosthetic materials to enhance their strength and make them impermeable to fluids. The coating applications of the invention make it possible to reinforce a weakened tissue such as an arterial wall.

The preferred proteins used in the present invention are structural proteins such as collagen and serum proteins such as albumin.

Collagen is the most abundant protein in the body. There are five types of collagen, each containing three polypeptides of about 1,000 residues per chain. The main functin of collagen is to maintain the shape and to resist the deformation of the tissues. In a similar fashion, the ropelike collagen fibrils help to enhance bond strength and to resist deformation in the tissue bonding or sealing composition of the present invention.

Another advantage of collagen is that when collagen is heated it can be denatured, and solubilised for easy application as a gelatin-like solution. When cooled, the collagen is partially renatured, resulting in a gel formation with excellent tensile strength. Heated collagen, therefore, is an ideal protein component in the present tissue bonding or sealing composition. Through heating, collagen can be solubilised and easily injected or applied, and by cooling it can be turned into a gel which provides both tensile strength and flexibility to the bond. Collagen can also be rendered in a sterile form. Moreover, albumin and collagen are more stable than their fibrin counterpart, both on the shelf and in vivo.

In addition, albumin and collagen when used in the present composition, provide distinct advantages over current procedures using "biological glues" which employ fibrin obtained from pooled blood samples. This exposes the recipient to the risk of infections from AIDS, Hepatitis A, Hepatitis non A and non B, Cytomegalovirus, Jakob-Creutzfeld disease, and others. The present composition containing human albumin on the other hand, while obtained from pooled blood products, does not expose the patient to these risks. Human albumin, unlike human fibrin, can be subjected to ultrafiltration techniques which results in a high yield of albumin free of infectious agents. Moreover, human albumin is more stable than its fibrin counterpart, both on the shelf and in vivo. This is because fibrin can be activated by thrombin and calcium, which are both present in the blood and other body tissues. Moreover, after its use, plasma fibrinolytic activity immediately begins to degrade the fibrin glue. As there is no enzyme system specifically designed to degrade albumin, its absorption will be slower than that of the fibrin glue counterpart.

Albumin is a transport protein with a molecular weight of 66,500 Daltons, and a half life of 15-20 days. It accounts for 70-80% of the colloid osmotic pressure of the plasma, and is distributed throughout the extracellular water. More than 60% of human albumin is located in the extravascular fluid compartments. It is, therefore, ideally suited for welding as it is present in most of the tissues which are to be welded, and will not cause a tissue inflammatory response. Moreover, its half life exceeds the time period necessary for wound strength to reach a level sufficient to resist normal stresses.

Because it is a transport protein, albumin binds naturally occurring therapeutic and toxic materials, as well as many pharmacologic agents. This property makes it ideal for bonding and sealing tissues, as well as bonding pharmacologic or other agents which need to be delivered to the wound sight in high concentrations. A detailed discussion of the binding characteristics of human serum albumin can be found in Thomas E. Emerson, Jr., "Unique Features of Albumin: A Brief Review" *Crit. Care Med.* vol. 17 no. 7 pp, 690-694 (July, 1989).

The preferred polysaccharide used in the composition of the present invention is hydroxypropylmethylcellulose which is preferably used in a sterile solution containing less than 10% of the active ingredient. As a sterile solution it may be formulated to have a molecular weight exceeding 80,000 daltons and a viscosity of at least about 4,000 centipoise. See, for example, Thomas J. Liesegang et al., "The Use of Hydroxypropyl Methyl Cellulose in Extracapsular Cataract Extraction with Intraocular Lens Implantation", *Am. J. Ophth.* vol. 102 pp. 723-726 (December, 1986).

The preferred group of compounds under the general class of proteoglycans and derivatives thereof as previously described are glycosaminoglycans which include hyaluronic acid and salts thereof, particularly sodium hyaluronate and chondroitin sulfate.

Hyaluronic acid is a polymer centered in the extracellular matrix of animals and humans. It is thought to form the filamentous backbone of both cartilage and other connective tissues.

Hyaluronic acid has a molecular weight of 4 to $80 \times 10^6$ Daltons. Structurally hyaluronic acid is characterized by repeating disaccharide subunits of sodium glucuronate linked to an N-Acetylglycosamine molecule by a B1→3 glucosidic bond. The disaccharide units are linked together with B1→4 glucosidic bond to form large polymers. Each subunit has one negative charge, which may help to explain its bond strength enhancing affect. (See *Principles of Biochemistry: Mammalian Biochemistry,* 7th edition, edited by Emil Smith et al., pp. 7 and 229 (1983).

Hyaluronic acid and its salts have other advantages. In its purified form, sodium hyaluronate has a viscosity of 40,000 centipoise at a shear rate of 2 sec.$^{-1}$ at 25° C., and over 200,000 centipoise at a shear rate of zero. This non-Newtonian, or pseudoplastic viscous property of hyaluronic acid makes it ideal for tissue welding. At high shear rates, such as occurs during injection through a syringe, the viscosity of hyaluronic acid is low, facilitating injection. This allows for its easy application to tissues. At low shear rates, such as after application to tissues, its viscosity is high. This helps to keep it localized to the tissue in the area to be welded or sealed.

Therefore, hyaluronic acid is ideally suited for tissue welding for two reasons. First, it helps to increase the tissue adhesive strength by providing a backbone for the protein component of the tissue adhesive material. Second, the pseudoplastic properties of hyaluronic acid provide it with ideal handling characteristics.

Chondroitin sulfate is a polymer centered in the extracellular matrix of animals and humans. It has a molecular weight of 22,500 daltons, and is composed of a repeating disaccharide subunit of glucuronic acid in Beta 1→3 linkage with N-Acetylgalactosamine. The subunits are then combined by Beta 1→4 linkage to form large polymers. Unlike hyaluronic acid, Chondroitin sulfate contains a double negative charge per repeating disaccharide unit, which may enhance bond strength in certain instances. This may help in the bonding and sealing of corneal tissue, which has the highest natural concentration of chondroitin sulfate of any tissue in the body.

Chondroitin sulfate, like hyaluronic acid, is highly viscous in concentrations of 50 mg/ml, where its viscosity is 4000 cps (at shear rate of 2 sec$^{-1}$, 25° C.). However, unlike hyaluronic acid, chondroitin sulfate is a Newtonian fluid, and does not change viscosity with changing shear rates. This property will allow it to remain localized more readily in areas where there are large shear forces during bonding.

The present invention may also include substances which alter the absorption characteristics of the composition so that the composition absorbs energy at lower energy levels. These substances reduce possible collateral damage to adjacent tissues typically associated with high energy level activators such as laser beams. See, "Mehmet C. Oz et al., "Tissue Soldering by Use of Indocyanine Green Dye-enhanced Fibrinogen with the Near Infrared Diode Laser", *J. Vasc. Surg.* vol. 11 no. 5 pp. 718-725 (May, 1990); and B. Jean et al., "Target Dyes In Ophthalmology - Parts I and II", *Lasers and Light in Ophthalmology* vol. 3 no. 1 pp 39-52 (1990). Dyes such as indocyanine, fluorescein and the like are particularly suited for this purpose. These dyes also may increase adhesivity, weld strength and viscosity. The dyes are preferably present in the composition in an amount of from about 0.01 to 50% by weight based on the total weight of the composition.

The addition of such dyes which have a peak light absorption at a specific wavelength, allows for the selective activation of the composition at the site of the weld or coating, while substantially reducing the risk of undesirable collateral thermal damage to adjacent tissues. By selecting a wavelength of light, emitted from a light source such as a laser beam, which matches the peak absorption wavelength of the dye used, a lower threshold of input energy is needed to obtain the desired tissue effect. This lower energy has little effect on untreated tissue. Thus, the energy is targeted only where the dye is applied or incorporated. As an example, indocyanine green is a dye that selectively binds to human or animal albumin and has a maximum absorbance at 805 nm in an albumin solution. When the dye is mixed with albumin, continuous wave diode laser light, which is commercially available at 808 nm wavelength, can be selectively used to heat and coagulate the ablumin. The selection of the peptide used as the first component is affected by the laser-dye combination desired. Peak absorption for indocyanine green in water solution is 770 nm. This does not match the output of the diode laser. The 805 nm peak is obtained in alubmin solution but not in solution with other proteins, such as fibrinogen. This effect is observed independent of albumin absorption which is low at 805 nm.

Other dye-laser combinations, include, but are not limited to, fluorescein isothiocyanate (Absorbance 490 nm) and an argon laser operating at 488–514 nm; silver compounds such as silver nitrate and a krypton laser (676 nm); dye compounds such as rose bengal, nile blue and Evans blue and Dye lasers absorbing in the range of 200 to 610 nm. Q-switch II ™ a dye obtained from Kodak, absorbs light from a Nd:YAG laser at 1064 nm and 1320 nm. Sudan III, Sudan black B and Indian Ink may also be utilized to selectively adsorb light from any of the above-mentioned lasers.

Non-coherent light sources such as infrared, ultraviolet or polychromatic white light may also be used.

EXAMPLE 1

0.55 ml of a 25% solution of human albumin obtained from the New York Blood Center was combined with 0.55 ml of hyaluronic acid and 5.5 mg of a sterile indocyanine green dye (Cardio-Green obtained from Becton-Dickinson). The resluting product was placed on corneosclera tissue as described below and exposed to a pulsed THC:YAG laser having a wave length of 2.15 um at an input level of 106 Joules and a pulse rate of 4 pulses per second.

The resulting weld was tested for normal preglue leaking pressure and post weld strength as follows.

Freshly enucleated porcine eyes were used to determine the strength of the bonding in closing corneoscleral cataract incisions similar to those used in cataract extraction surgery. A 64 beaver blade was used to make a 5–10 mm partial thickness scleral incision, 1–3 mm posterior to the limbus. The incision was extended anteriorly into clear cornea, and a superblade was used to enter the anterior chamber. A 25 G butterfly syringe was inserted into the anterior chamber through clear cornea, and was attached to a water column of Dextrose 5% Normal Saline solution.

The water column was elevated until leakage was noted at the wound margin. The process was repeated at least three times until reproducible-results were obtained. The glue was then applied and congealed with the laser to form a firm seal. The water column was then elevated until leakage could be visualized around the glue margin, which is reported as the bursting pressure. If the bursting pressure was near the baseline values, additional glue was applied to the area of leakage, and additional laser energy was applied. If this resulted in a stronger bond, this valve was reported as the bursting pressure.

The results are shown in Table 1. It will be noted that viscosity was measured subjectively on a scale of 1–10 wherein a viscosity of 1 was characterized by a flowable liquid such as water, a viscosity of 5–8 is similar to honey and a viscosity of 10 was characteristic of a gel-like substance.

TABLE 1

| | |
|---|---|
| Hyaluronic Acid 10 mg/ml | 0.55 ml |
| 25% Human Albumin | 0.55 ml |
| Indocyanine green dye | 5.5 mg |
| Incision Length | 9 mm |
| Distance from limbus | 2 mm |
| Normal Pre-Glue Bursting pressure | 4 in. $H_2O$ |
| Post-Welding Bursting pressure | 60 in. $H_2O$ |
| Viscosity | 7 |

EXAMPLE 2

The same composition was prepared as in Example 1 except that the indocyanine green dye was omitted. The sample was placed on tissue specimens and activated as described in Example 1. The results are shown in Table 2.

TABLE 2

| | |
|---|---|
| Hyaluronic Acid 10 mg/ml | 0.75 ml |
| 25% Human Albumin | 0.75 ml |
| Incision Length | 9 mm |
| Distance from limbus | 2 mm |
| Normal Pre-Glue Bursting pressure | 4 in. $H_2O$ |
| Post-Welding Bursting pressure | >60 in. $H_2O$ |
| Viscosity | 7 |

EXAMPLES 3–9

Seven samples of the composition of the present invention were prepared by combining sodium hyaluronate (Healon manufactured by Pharmacia Inc and Amvisc Plus manufactured by Med Chem Products, Inc.) and a mixture of 25% human albumin which contained 10 mg/ml of indocyanine green dye. The mixtures were refrigerated overnight to allow for adequate mixing.

The mixtures were applied to tissues in the same manner as described in Example 1 and exposed to a diode laser manufactured by Spectre Physics at a wavelength of 808 nm at an energy output of 300–450 milliwatts and a power density of 12 watts/$cm^2$ and a spot size of 2 mm.

On application of the laser energy an area of whitening occurred, and then congealed. After adequate laser application, the glue set in a fashion similar to that seen with commercially available rubber cement. The elastic properties of the glue could be modulated by additional laser energy. As more energy was applied, firmer, less flexible, stronger bonds could be formed. At lower energy levels, the bond was more elastic. Over time, when allowed to dry further, both types of bonds appeared to become stronger. However, total drying results in a brittle, friable material and is undesirable.

The samples were tested as described in connection with Example 1 and the results are shown in Table 3.

TABLE 3

| Sample | Healon (Parts) | 25% Human Albumin with 10 mg/ml of ICG dye (Parts) | Incision Length (mm) | Distance from limbus (mm) | Normal Pre-Glue Bursting pressure (Inches $H_2O$) | Post-Welding Bursting pressure (Inches $H_2O$) | Viscosity |
|---|---|---|---|---|---|---|---|
| 3 | 10 | 1 | 9 | 2 | 2 | 4 | 10 |
| 4 | 5 | 1 | 8 | 2 | 2 | 16 | 10 |
| 5 | 2 | 1 | 9 | 2 | 4 | 52 | 8 |
| 6 | 1 | 1 | 10 | 2 | 2 | 40 | 7 |
| 7 | 1 | 2 | 10 | 2 | 2 | 10 | 6 |
| 8 | 1 | 5 | 9 | 2 | 6 | 30 | 2 |
| 9 | 1 | 10 | 9 | 2.5 | 4 | 10 | 1 |

To determine if the low dye concentration in sample 3 was responsible for its lower bond strength a dye concentration similar to that in sample 9 was made. Healon 0.55 ml was mixed with 25% human albumin (0.051 ml) and 5.0 mg of indocyanine green dye. In this example the higher concentration of dye was not found to improve the strength of the bond formed with a 10 parts Healon to 1 part 25% human albumin with 10 mg/ml of indocyanine green dye mixture, indicating that the low dye concentration in sample 3 was not responsible for the lower bond strength. It is believed that the high Healon to albumin ratio in sample 3 was responsible for its lower tensile strength.

EXAMPLE 10

0.8 ml of Amvisc Plus, 0.8 ml of 25% human albumin and 0.2 ml of a 2.5 mg/ml sterile solution of Cardio-Green were mixed and then applied to tissues and exposed to laser energy in the same manner as described in Examples 3-9. The results are shown in Table 4.

TABLE 4

| AmvisPlus | 1 part |
|---|---|
| 25% Human Albumin | 1 part |
| Incision Length | 6 mm |
| Distance from limbus | 2.5 mm |
| Normal Pre-Glue Bursting pressure | 4 in. $H_2O$ |
| Post-Welding Bursting pressure | 41 in. $H_2O$ |
| Viscosity | 7 |

EXAMPLE 11

0.5 ml of a 2% hydroxypropylmethylcellulose solution (Occucoat manufactured by Lederle Laboratories), 0.5 ml of 25% human albumin and 0.1 ml of a 2.5 mg/ml sterile solution of Cardio Green was tested and exposed to laser energy in the same manner as in Examples 3-9. The results are shown in Table 5.

TABLE 5

| Occucoat | 1 part |
|---|---|
| Albumin | 1 part |
| Incision Length | 7 mm |
| Distance from limbus | 2 mm |
| Normal Pre-Glue Bursting pressure | 8 in. $H_2O$ |
| Post-Welding Bursting pressure | 32 in. $H_2O$ |
| Viscosity | 2 |

EXAMPLES 12-15

Four samples of the composition of the present invention containing the components and amounts identified in Table 6 were tested and exposed to laser energy in the same manner as described in Examples 3-9. The results are shown in Table 6.

TABLE 6

| Sample | | 25% Human Albumin with 10 mg/ml of ICG dye (Parts) | Incision Length (mm) | Distance from limbus (mm) | Normal Pre-Glue Bursting pressure (Inches $H_2O$) | Post-Welding Bursting pressure (Inches $H_2O$) | Viscosity |
|---|---|---|---|---|---|---|---|
| 12 | Viscoat (Parts) 1 | 1 | 7 | 3.0 | 6 | 13 | 8 |
| 13 | Honey (Parts) 1 | 1 | 7 | 3.0 | 4 | 20 | 3 |
| 14 | Silicone (Parts) 1 | 1 | 10 | 2.0 | 2 | 8 | 2 |
| 15 | 15% Dextran solution (Parts) 1 | 1 | 10 | 2.5 | 4 | 40 | 3 |

EXAMPLE 16

A mixture of emulsified pig vitreous (1.5 ml) composed primarily of sodium hyaluronate and collagen was combined with 0.1 ml of a sterile solution of Cardio-Green. The mixture was tested and exposed to laser energy as described in connection with Examples 3-9. The results are shown in Table 7.

TABLE 7

| Incision Length (mm) | Distance from limbus (mm) | Normal Pre-Glue Bursting pressure (Inches H2O) | Post-Welding Bursting pressure (Inches H2O) | Viscosity |
|---|---|---|---|---|
| 7 | 2 | 4 | 13 | 6 |

EXAMPLE 17

2.0. ml of synthetic glycerine (manufactured by HUMCO Labs) was combined with one ml of a mixture of 25% human albumin solution containing a sterile solution of Cardio-Green in a concentration of 10 mg/ml. The sample was tested and exposed to laser energy in the same manner as described in Examples 3–9. The results are shown in Table 8.

TABLE 8

| Glycerine | 2 parts |
|---|---|
| 25% Human Albumin with 10 mg/ml of ICG dye | 1 part |
| Incision Length | 9 mm |
| Distance from limbus | 2 mm |
| Normal Pre-Glue Bursting pressure | 22 in. H2O |
| Post-Welding Bursting pressure | 32 in. H2O |
| Viscosity | 3 |

EXAMPLES 18–21

Freshly harvested rat skin was trimmed into srips and the edges of two strips brought into approximation. The adhesive mixtures shown in Table 9 was then topically applied. Energy was input until tissue soldering was effected to produce a weld of about 1 mm. Immediately after completion of the repair, weld length and break point (in g) was measured. Samples 18–20 and control samples A, C and D were exposed to the same laser and under the same conditions described in connection with Examples 3–9. Control sample b and sample 21 were exposed to high frequency electrical diathermy (13.5 MHz electrocautery). The results are shown in Table 9.

TABLE 9

| Sample | Composition | Mean Tensile Strength (g/cm2) |
|---|---|---|
| Control A) | indocyanine green 0.5% | <100 |
| Control B) | none | <100 |
| Control C) | human fibrinogen 70% + indocyanine green 0.5% | 113 |
| Control D) | human albumn 25% + indocyanine green 0.5% | 250 |
| 18 | human albumin 12% sodium hyaluronate 0.5% + indocyanine green 0.5% | 441 |
| 19 | human albumin 25% dextran 15% + indocyanine green 0.5% | 386 |
| 20 | bovine collagen 13% sodium hyaluronate 0.3% + indocyanine green 0.5% | 531 |
| 21 | human albumin 8% sodium hyaluronate 0.7% | 514 |

As shown in Table 9, compositions of the present invention exhibited a mean tensile strength far exceeding the tensile strength of the protein (human fibrinogen or albumin) alone.

EXAMPLE 22

A composition in accordance with the present invention was tested on three patients in accordance with the following. The patient population comprised end-stage renal disease patients requiring arteriovenus fistula for vascular access for hemodialysis. Consent for experimental treatment was obtained under an approved Institutional Review Board protocol. Using standard techniques the radial artery and a suitable forearm vein were isloated. 6–7 mm anastomoses were created between the artery and vein using a loop of 6 mm Gortex (TM) graft (standard wall). In one group of patients, this was reinforced with a glue mixture of 25% albumin (New York Blood Center) and a 10 mg/ml solution of Healon (Pharmacia) in a 1:2 combination, with the addition of Fluorescein dye (2 gtts, 5 mg/ml). The glue was sealed to the edge of the anastomosis and suture holes using a KTP laser (532 nm, 1 mm spot size, 500 mW).

The other group of patients received no laser or glue treatment after completion of the sutured anastomosis. After unclamping, any blood leaking from the anastomosis was removed from the field with gauze sponges until bleeding ceased. By subtracting the initial weight of these sponges from the weight after use, the total blood loss from each anastomosis was obtained. The bleeding time was recorded as well and the results are shown in Table 10.

TABLE 10

| Mean Blood Loss | Mean Bleeding Time |
|---|---|
| Treatment Group - Gortex AVF with composition. | |
| 14.7 g | 4 min |
| Control Group - Gortex AVF without composition | |
| 24.0 g | 4 min |

Overall, the bleeding time was significantly reduced with the composition of the present invention. As expected, the time to from a clot in any unsealed holes remained the same in the treatment and control groups.

What we claim is:

1. A composition for bonding separated tissues together or for coating tissues or prosthetic materials comprising:
   (a) at least one first component in an amount of at least 4.2% by weight based on the total weight of the composition, said first component being selected from the group consisting of naturally occurring peptides, synthetic peptides, and mixtures thereof; and
   (b) At least one second component adapted to support the first component to form a matrix, sol or gel with the first component.

2. The composition of claim 1 wherein the peptides are selected from structural proteins and serum proteins and mixtures thereof.

3. The composition of claim 1 wherein the amount of the peptide is in the range of from 4.2% to 70% by weight.

4. The composition of claim 3 wherein the amount of peptide is from about 8 to 35% by weight.

5. The composition of claim 1 wherein the second component is selected from proteoglycans, saccharides, polyalcohols and mixtures thereof.

6. The composition of claim 5 wherein the second component is at least one glycosaminoglycan.

7. The composition of claim 6 wherein the glycosaminoglycans are selected from natural or synthetic non-cellular body matrix materials found in the interstices between cells.

8. The composition of claim 7 wherein said body matrix materials are selected from hyaluronic acid, salts of hyaluronic acid, chondroitin sulfate, dermatin sulfate, keratin sulfate and heparin sulfate.

9. The composition of claim 5 wherein the saccharides are selected from fructose, hydroxypropylmethylcellulose, dextrans and agarose.

10. The composition of claim 5 wherein the polyalcohol is glycerine.

11. The composition of claim 6 wherein the amount of the glycosaminoglycans is in the range of about 0.1 to 20% by weight.

12. The composition of claim 5 wherein the amount of the saccharides is in the range of from 0.1 to 70% by weight.

13. The composition of claim 5 wherein the amount of the polyalcohol is in the range of from about 10 to 90% by weight.

14. The composition of claim 1 further comprising at least one additive selected from a viscosity modifier and bonding enhancer 15. The composition of claim 14 wherein the additive is present in an amount of no more than about 65% by weight.

16. The composition of claim 1 wherein the composition is adapted to bond separated tissues together and has a viscosity in the range of from about 1,000 to 1,000,000 centipoise.

17. The composition of claim 1 wherein the composition is adapted to coat said tissues or prosthetic materials and has a viscosity in the range of from about 100 to 1,000 centipoise.

18. A composition for bonding separated tissues together or for coating tissues or prosthetic materials comprising:
(a) at least one first component selected from the group consisting of albumin, α-globulins, β-globulins, γ-globulins, transthyretin, collagen, elastin, fibronectin, fibrinogen, fibrin, and thrombin in an amount of at least 4.2% by weight based on the total weight of the composition; and
(b) at least one second component adapted to support the first component to form a matrix, sol or gel with the first component.

19. A composition for bonding separated tissues together or for coating tissues or prosthetic materials comprising:
(a) at least one first component in an amount of at least about 1.0% by weight based on the total weight of the composition, said first component being selected from the group consisting of naturally occurring peptides, synthetic peptides and mixtures thereof;
(b) at least one second component adapted to support the first component to form a matrix, sol or gel with the first component; and
(c) at lest one energy absorbing compound.

20. The composition of claim 19 wherein the energy absorbing compound is selected from indocyanine and fluorescein.

21. The composition of claim 19 wherein the energy absorbing compound is present in an amount of from about 0.1 to 50% by weight.

22. A composition for bonding separated tissues together or for coating tissues or prosthetic materials comprising:
(a) albumin, fibrin, fibrinogen or collagen in an amount of 8-35% by weight;
(b) hyaluronic acid, sodium salts thereof, or chondroitin sulfate in an amount of 0.1-20% by weight, said composition having a viscosity in the range of from about 1,000 to 200,000 centipoise; and
(c) an energy absorption altering compound selected from indocyanine and fluorescein in an amount of from about 0.01-10% by weight.

* * * * *